United States Patent [19]

Richardson

[11] Patent Number: 5,752,506
[45] Date of Patent: May 19, 1998

[54] VENTILATOR SYSTEM

[75] Inventor: Peter Richardson, Sandy, Utah

[73] Assignee: Bunnell Incorporated, Salt Lake City, Utah

[21] Appl. No.: 700,840

[22] Filed: Aug. 21, 1996

[51] Int. Cl.$^6$ .................................................. A61H 31/00
[52] U.S. Cl. .................... 128/204.18; 128/204.21
[58] Field of Search ..................... 128/204.18, 204.21, 128/204.25, 204.26, 203.12, 203.25, 205.24, 207.15, 207.16, 910, 911

[56] References Cited

U.S. PATENT DOCUMENTS

| | | |
|---|---|---|
| 4,471,773 | 9/1984 | Bunnell et al. . |
| 4,481,944 | 11/1984 | Bunnell . |
| 4,520,812 | 6/1985 | Freitag et al. . |
| 4,538,604 | 9/1985 | Usry et al. . |
| 4,565,194 | 1/1986 | Weerda et al. . |
| 4,573,462 | 3/1986 | Baum . |
| 4,723,543 | 2/1988 | Beran . |
| 4,815,459 | 3/1989 | Beran . |
| 5,181,508 | 1/1993 | Poole, Jr. . |
| 5,207,220 | 5/1993 | Long . |
| 5,239,994 | 8/1993 | Atkins . |
| 5,287,851 | 2/1994 | Beran et al. . |
| 5,309,903 | 5/1994 | Long . |

OTHER PUBLICATIONS

Paper entitled "American National Standard for Medical Materiel—Luer Taper Fittings—Performance" pp. 7–15, 1983.

Paper entitled "Standard Specification for Conical Fittings of 15 mm and 22 mm Sizes" pp. 1–8.

Paper entitled "Standard Specification for Tracheal Tube Connectors" pp. 1–3.

Package Insert for Porex Jet Ventilator adaptor. Undated.

*Primary Examiner*—Vincent Millin
*Assistant Examiner*—Robert N. Wieland
*Attorney, Agent, or Firm*—Trask, Britt & Rossa

[57] ABSTRACT

A ventilation system for use in ventilating a patient includes a source of pressurized gas, a primary delivery conduit to communicate and transmit the pressurized gas, an endotracheal tube for insertion into the patient's mouth and throat, and an adapter. The adapter includes a first side aperture and a second side aperture, coupled between the primary delivery conduit and the endotracheal tube for communication pressurized gas therebetween. A pressure detector is connected to the first side aperture to detect and generate signals reflective of the pressure of gas in the adapter. An indicator associated with the pressure detector receives the signals and visually displays an indication of the detected pressure of the gas in the adapter. The second side aperture receives and communicates pulses of pressurized gas from the source of pressurized gas to the endotracheal tube. The side apertures are connected to channels that angle toward the second part. The adapter may be formed from a separate base and top joined together. A source of lung therapy material may also be included in the system.

51 Claims, 13 Drawing Sheets

VENTILATOR SYSTEM

BACKGROUND OF THE INVENTION

1. Field of the Invention

This invention relates to a ventilation system for supplying gas to a person's respiratory system. More particularly, the ventilation system includes an adapter to interconnect a source of gas, an endotracheal tube, a pressure sensor, and a pressure indicator.

2. State of the Art

In conventional ventilators, oxygen or air is introduced into and removed from a person's respiratory system at rates that generally coincide with the normal respiration rate of the person. Some conventional ventilators automatically apply the oxygen or air at fixed time intervals or trigger the application of oxygen and air by sensing respiratory effort.

Some patients may benefit from the application of rapid or high frequency, positive pressure pulses of oxygen and air to their respiratory system. These devices, called rapid-pulse or high frequency ventilators, are employed to deliver positive pressure pulses of gas to patients at a higher than normal rate of inhalation and exhalation. For example, the positive pressure pulses may be delivered at rates from 240 pulses per minute to 660 pulses per minute.

Both conventional and rapid-pulse or high frequency ventilators are accepted modalities available to address different presenting symptomology. In order to make both modalities available, separately or in combination, ventilators which combine the features of the conventional and rapid-pulse ventilators are desirable.

A combination rapid-pulse/conventional ventilator is disclosed in U.S. Pat. No. 5,239,994 (Atkins), a series of gas pressure pulses are applied to a patient's respiratory system through a gas jet nozzle. The gas jet nozzle is disposed in one end of an endotracheal tube. The other end of the endotracheal tube is for insertion into the patient's trachea. Air and oxygen are supplied from separate sources, combined, and later heated and humidified to a desired temperature and relative humidity. The mixed gases then flow through a primary delivery conduit via a manifold to the gas jet nozzle. A secondary delivery conduit connects the primary delivery conduit to the endotracheal tube at a location near the gas jet nozzle. Coupled to the manifold is an exhaust conduit in which the person's expired gas flow can be eliminated and measured. To detect pressure in the tracheal conduit, a pressure detector is coupled by way of a connecting tube to a pressure monitoring side lumen formed in the endotracheal tube.

In the past, such combination ventilators required special endotracheal tubes having a pressure monitoring side lumen to measure the pressure of gas flowing toward the patient. Thus, gas delivery and airway pressure monitoring could not be accomplished through a standard (single-lumen) endotracheal tube.

SUMMARY OF THE INVENTION

A ventilation system includes a source of pressurized gas and a primary delivery conduit, a first end of which is connected to the source of gas. An adapter, having a first end, a second end, a first side aperture, a second side aperture, and a central channel, is connected at its first end to a second end of the primary delivery conduit via a receiver.

The adapter further includes a first port, formed at the first end, for receiving the gas from the primary delivery conduit and communicating the gas to the central channel. An endotracheal tube has both an internal or distal end for placement in the trachea of the patient and an external or proximal end. The external end is connected to the second end of the adapter. A second port, formed at the second end of the adapter, communicates with the central channel and transmits the gas from the source of gas to the endotracheal tube during inhalation.

An exhaust conduit, having two ends, is connected at one end to the first end of the adapter via the receiver or, alternately, to the primary delivery conduit. During expiration by the patient, exhaled gases flow through the endotracheal tube and central channel, and out of the ventilation system via the exhaust conduit.

Pressure detecting means is connected to be in fluid communication with the first side aperture to detect the pressure of the gas in the central channel. A pressure monitoring port is formed at the first side aperture and provides a conduit through which pressure detection means can be associated to detect the pressure of the gas flowing through the adapter and the endotracheal tube. The pressure detecting means supplies signals reflective of the detected pressure to indicating means which receive the signals and processes them into a visual display of the detected pressure of the gas.

The second side aperture receives and communicates pulses of gas to the adapter for further communication to the second port and endotracheal tube. Preferably, a ventilation conduit, disposed between the second side aperture and the central channel, is included to communicate gases therebetween. It should be understood that the term gas, as used in this disclosure, means any fluid-like material which is suitable for introduction into the lungs of the patient in the practice of a ventilation modality or therapy. It should also be understood that the term patient principally refers to a person but may also include any animal that would require ventilation therapy.

In an alternative configuration of the invention, a control unit is coupled to the primary delivery conduit for selectively varying the flow rate through the adapter. The control unit includes a secondary delivery conduit coupled between the primary delivery conduit and the second side aperture for delivering gas under pressure. The control unit also includes a valve disposed in the secondary delivery conduit and responsive to control signals for varying the pressure of gas flowing through the secondary delivery conduit and to the endotracheal tube. A control signal source selectively produces control signals for supply to the valve to control the variation of pressure of gas flowing through the secondary delivery conduit.

Another alternative configuration contains a variable restrictor which is operated under control of a controller, such as a microprocessor, to control the base flow of gas toward the first port.

In a preferred alternative, the cross-sectional area of the ventilation conduit is larger than the cross-sectional area of the pressure monitoring conduit. Even more preferably, the pressure monitoring conduit communicates with the central channel at a position closer to the second port than the position at which the ventilation conduit and the central channel communicate.

In a highly preferred arrangement, the adapter has a base and top that are assembled to form the adapter. Grooves and alignment structure are provided to facilitate connection and to define the pressure monitoring channel and the ventilation channel which enter the central channel spaced from each other radially and axially and at selected angles.

In another alternative embodiment, the adapter of the invention includes a first outer edge extending from the first side aperture and a second outer edge extending from the second side aperture. A locking mechanism can be connected to the second outer edge for securely associating the source of gas to the second side aperture. Likewise, a locking mechanism can be connected to the first outer edge in order to securely associate the pressure detecting means to the first side aperture. Locking mechanisms for use in the invention include clasps, threaded connectors such as "Luer-Lock" devices, or any other means known in the art for securely associating a conduit to an aperture.

In an alternative arrangement, a source of lung therapy material may be provided and connected with or without the use of restrictors to supply such material for entrainment in the pressurized gas.

In a preferred configuration, the adapter may have separate sources of gas for the first port and the second side aperture. Alternatively, the gas may be supplied only through the second side port at a high frequency rate and the first port may be open to the atmosphere. The adapter may also be provided separate from a system.

BRIEF DESCRIPTION OF THE DRAWINGS

In the drawings which illustrate what is presently regarded as the best mode of the invention.

DESCRIPTION OF THE PREFERRED EMBODIMENTS

Figure 1:
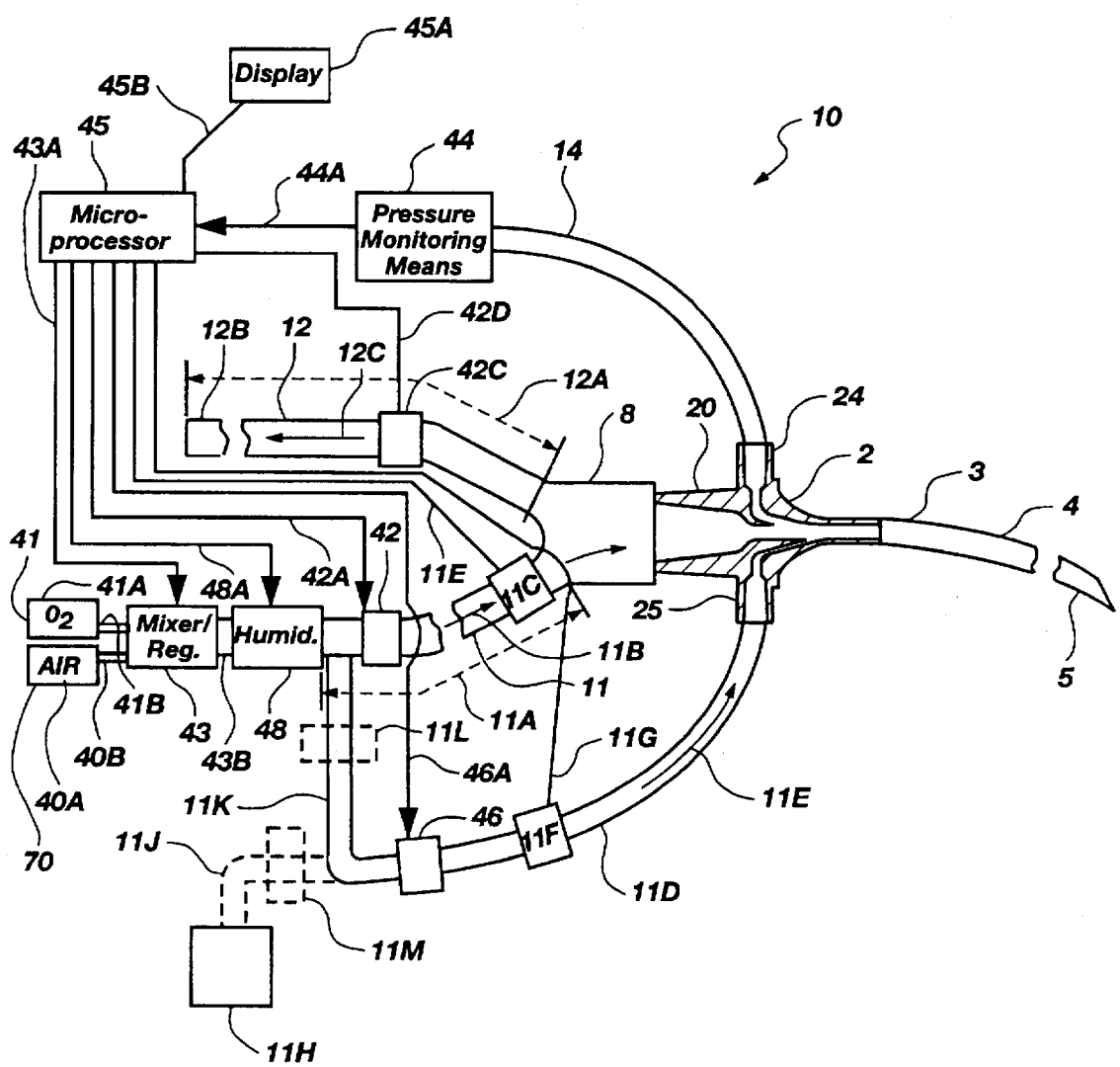
FIG. 1 is a schematic diagram of the ventilator system of the invention.

FIG. 1 is a schematic diagram of a ventilation system 10 for use in performing ventilation modalities or therapies on a patient. The ventilation system 10 applies breathable material to a patient's respiratory system by way of an adapter 2. The adapter 2 is disposed in one end 3 of an endotracheal tube 4. The other end 5 of the endotracheal tube 4 is for insertion through the patient's mouth or nose and into the patient's trachea (intubation). The endotracheal tube 4 is formed in a variety of sizes and shapes so as to facilitate intubation. The endotracheal tube 4 may also contain various pressure and temperature detectors not shown or here discussed in detail.

The ventilation system 10 of FIG. 1 further includes a source 40 of air 40A which is preferably medical grade air with approximately 21 percent oxygen, and 79 percent nitrogen, and a source 41 of oxygen 41A, respectively. The air 40A is stored or available under pressure (above ambient pressure) sufficient to provide for desired flow of air 40A in operation.

The system 10 also has a separate oxygen source 41 which contains medical grade (breathable) oxygen 41A under pressure sufficient to provide for desired flows of oxygen 41A to the patient. The oxygen source 41 can be operated to enrich the concentration of oxygen in the air 40A being supplied from the air source 40. Exemplary gas sources, providing a mixture of air and oxygen and suitable for use in the present invention, are described in U.S. Pat. No. 5,239,994, the disclosure of which is incorporated herein by reference.

It may be noted that other gas mixtures may be used for different purposes. That is, different breathable material involving different combinations of gas and liquids may be supplied for different therapies or purposes. Mixtures involving the use of helium, nitrogen, and nitric oxide are within contemplation.

The gas from sources 40 and 41 is supplied to a mixer and regulator 43 (such as a Bird Blender) via conduits 40B and 41B. The air 40A and oxygen 41A are mixed in the mixer and regulator 43 to a specific concentration (ranging from 100 percent air to 100 percent oxygen, depending on the patient's blood gas levels and level of hypoxia). The mixture is regulated to a predetermined constant supply pressure of, for example, about 10 psi, as directed by the user through the microprocessor 45 via conductor 43A. The mixed gas is then preferably supplied to humidifier 48 via conduit 43B where it is heated and humidified to a desired temperature and humidity of, for example, 37 degrees Centigrade and 100 percent relative humidity. The desired temperature and humidity is selected by a user through operation of microprocessor 45 which supplies control signals via conductor 48A to the humidifier 48. Alternatively, the temperature and humidity can be preprogrammed or preset.

The heated and humidified gas then flows from the humidifier 48 into primary delivery conduit 11. The primary delivery conduit 11 is sized in length 11A to be connected to and in fluid communication with a receiver 8. The receiver 8 is formed to and connects the delivery conduit 11 to the adapter 2.

A receiver 8 is here shown sized to fit snugly and sealingly over the first end 20 of the adapter 2 so that breathable material (e.g., air and/or oxygen) may pass into the adapter 2. The receiver 8 may also be sized to fit sealingly and snugly into the first end of the adapter 2. Further, various clamps, locking connections or friction connections may be used to connect the conduit 11 to the receiver 8 and the receiver to the first end 20. Alternatively, the conduit 11 and the receiver 8 may be unitarily formed as desired.

Figure 2:
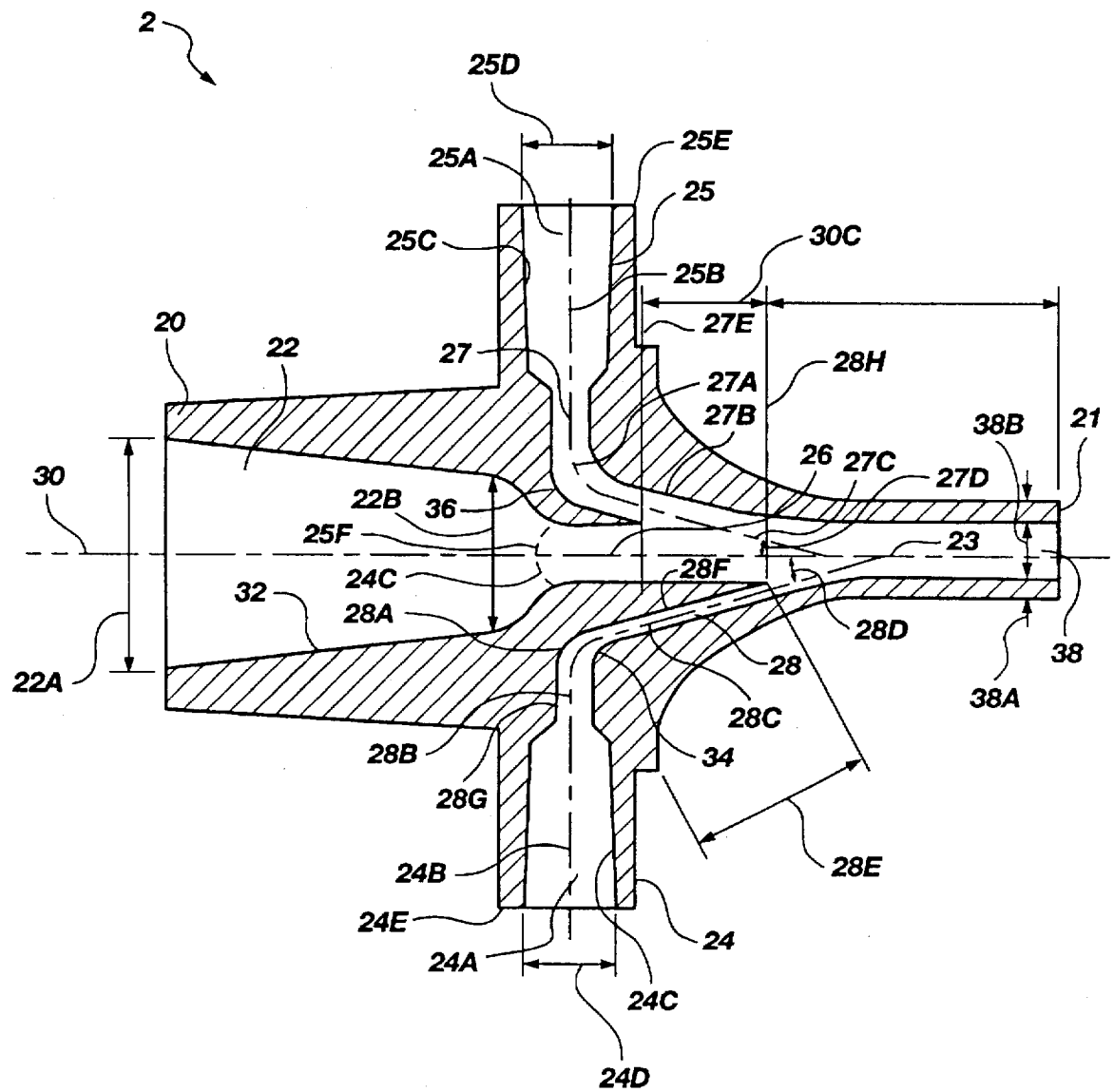
FIG. 2 is a cross-sectional diagram of an adapter for use in the system of FIG. 1 of the invention.

FIG. 2 is an enlarged cross-sectional view of the adapter 2. The adapter 2 includes a first end 20 having a first port 22 and a second end 21 having a second port 23. The first port 22 may be of any desired size to provide for connection to the receiver 8 or to a conduit. In practice, the first port 22 may be sized for standard tubing such as tubing having a diameter of 22 mm, 15 mm, 10 mm and 8.5 mm. The second port 23 is preferably sized to fit a selected endotracheal tube having an internal diameter of, for example, 2.5 mm, 3 mm, 3.5 mm and the like.

A central channel 26 is disposed between and in direct communication with the first port 22 and the second port 23. As can be seen, the first port 22, the second port 23 and the control channel 26 are formed along a common or central axis 30.

The second port 23 is here shown with an opening 38 smaller in cross section than that of the first port 22. In the illustrated embodiment, the opening 38 has an exterior diameter 38A at the second end 21 from about 2 mm to about 6 mm. The interior opening 38 may be circular in cross section and have a diameter 38B from about 6 mm to about 9 mm. The second end 21 is formed and sized to snugly and sealingly insert into the one end 3 of the endotracheal tube 4. Other connecting arrangements may be used or desired.

As here shown, the first port 22 has an interior with a conical shape. The first port diameter 22A is about 12 mm. The interior wall 32 tapers with the internal diameter 22B decreasing as desired and as here shown to about 6-8 mm. The conical shape of the first port 22 facilitates the internal connection of tapered connectors associated with various shapes and sizes of receivers such as receiver 8.

Returning to FIG. 1, the primary delivery conduit 11 and an exhaust conduit 12 are both connected to the receiver 8 and preferably unitarily formed therewith. That is, the receiver 8 is unitarily formed with an exhaust conduit 12 that is sized in length 12A a distance selected so the distal end 12B is preferably positioned to direct the exhaled material away from the patient and others in close proximity to the patient.

The exhaust conduit 12 may also contain an exhaust variable restrictor 42C which can be preset or operated to regulate by increasing or decreasing the flow of gas passing 12C through the exhaust conduit 12. The exhaust variable restrictor 42C may consist of a valve, orifice, external clamp or any other device that incrementally or adjustably is operable to increase or decrease the cross-sectional area of the exhaust conduit 12 and, in turn, regulate or restrict the flow of material therethrough. The exhaust variable restrictor 42C is preferably an electrically operated device such as a conventional solenoid valve. The variable restrictor 42C is operated by and under control of microprocessor 45 (such as a Motorola 6809) via conductor 42D to open or close as desired to obtain a desired pressure and or flow rate of breathable material to the patient.

After being humidified and heated in the humidifier 48, the mixture of air 40A and oxygen 41A is supplied under pressure toward 11B receiver 8 through variable restrictor 42 and pressure regulator 11C. By operating the microprocessor 45, a signal is sent via conductor 42D to close the exhaust variable restrictor 42C and via conductor 46A to close variable restrictor 46. In turn, the flow of gas through the exhaust conduit 12 and secondary conduit 11D is intermittently shut or closed. Thus, the gas mixture 40A and 41A is forced into receiver 8. Once diverted, the mixture of oxygen 41A and air 40A flows via the central channel 26, through the distal port 23, and towards the endotracheal tube 4 which has been inserted into the patient, thus forcing mixed gases into the patient's lungs.

Upon opening exhaust variable restrictor 42C and closing variable restrictor 42 by sending signals via conductors 42D and 42A, respectively, exhaled gases from the patient flow in reverse order through the endotracheal tube 4, second port 23, central channel 26, and first port 22 to eventually exit the system via the exhaust conduit 12. In this manner, conventional ventilation is accomplished at normal respiration rates (e.g., 15 breaths/min.). The pressure regulator 11C may be preset or may be electrically operable by the microprocessor 45 via conductor 11E to supply gases at conventional pressures of, for example, 1 to 2 pounds per square inch (psi).

The adapter of FIG. 2 also includes two side ports 24 and 25. Both ports 24 and 25 are cylindrically shaped one with first side aperture 24A and the other with second side aperture 25A. As here shown, the ports 24 and 25 are placed normal to the central channel 26 and more particularly the axis 30.

Figure 3:
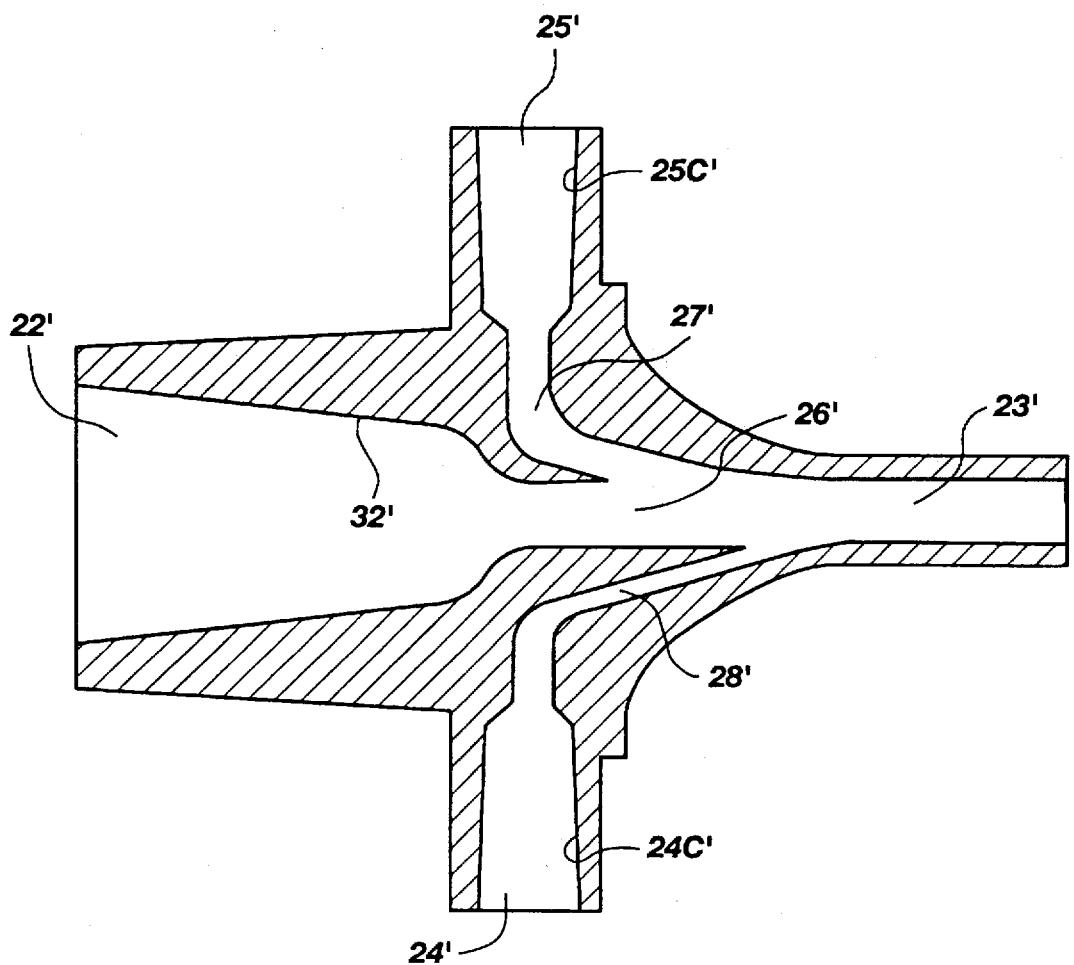
FIG. 3 is a cross-sectional diagram of another embodiment of an adapter for use in the system of FIG. 1.
Figure 4:
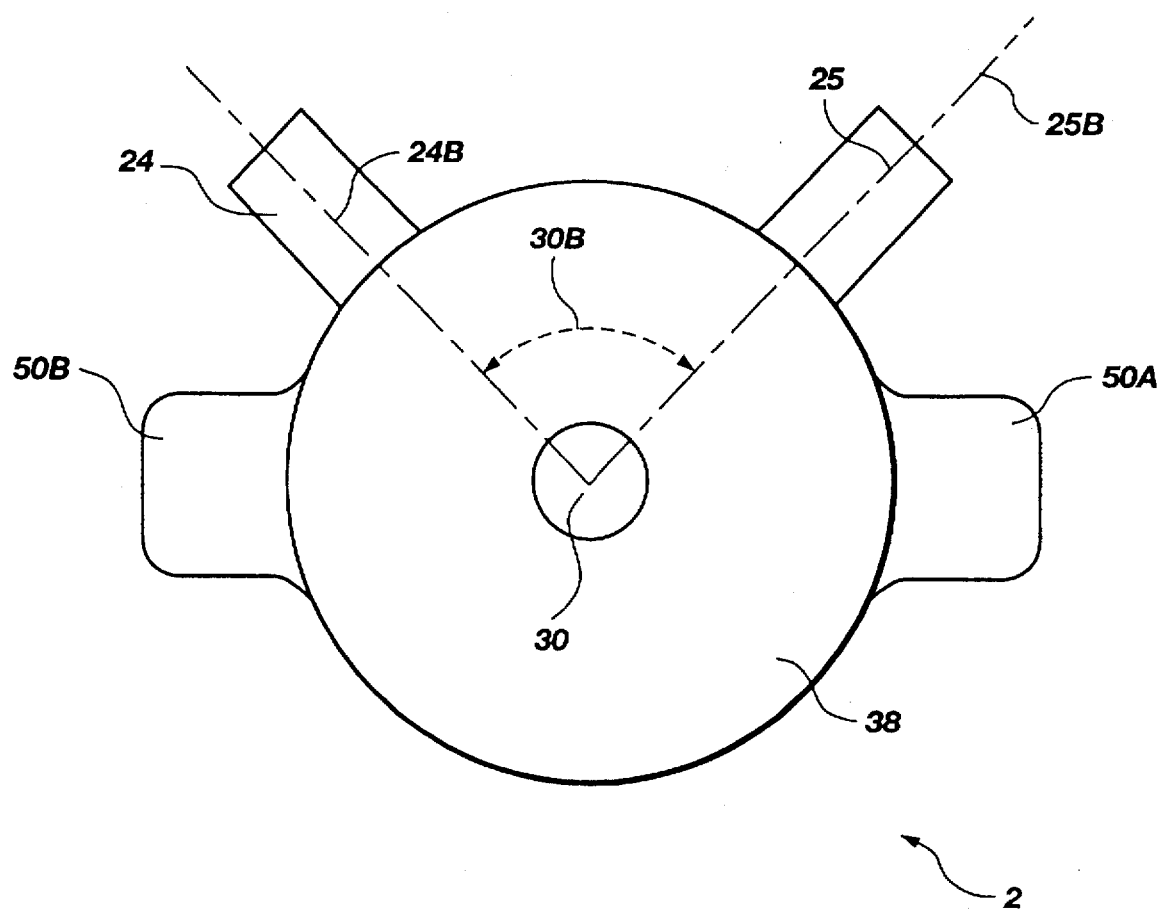
FIG. 4 is an enlarged frontal view of the adapter of FIG. 2.
Figure 5:
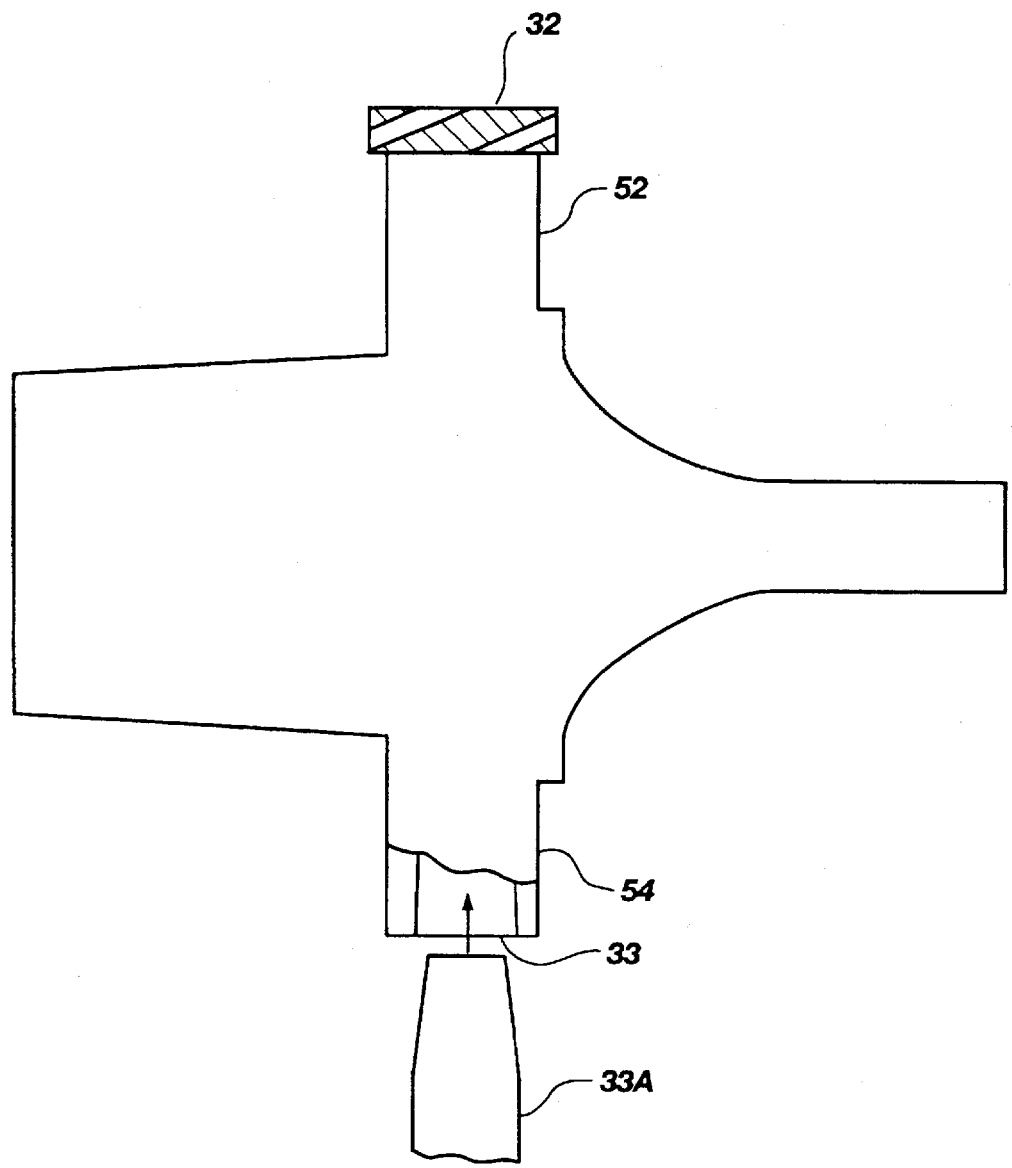
FIG. 5 is a side view of another embodiment of the adapter for use in the system of FIG. 1.

The apertures 24A and 25A may have any convenient or desired geometrical orientation relative to the central channel 26 and axis 30. The first side aperture 24 and the second side aperture 25 are each positioned about the axis 30 of the central channel 26 and are spaced radially apart in relation to each other, as illustrated in FIG. 4. That is, the port 24 has an axis 24B which when extended intersects axis 30 at about a 90 degree angle 24C. Similarly, the port 25 has an axis 25B which when extended also intersects axis 30 at a 90 degree angle 25F. When viewed along axis 30, however, the axis 24B and axis 25B and in turn ports 24 and 25 are radially spaced apart as necessary to facilitate connecting conduits as hereinafter discussed. The radial spacing 30B may be from about 90 degrees as shown in FIG. 4 to about 180 degrees as shown in FIGS. 2 and 3 and 5.

As seen in FIG. 2, the second side aperture 25 consists of a conically shaped interior surface 25C, having an inside diameter 25D of about 4 mm at the outer end 25E, for receiving a tapered connector of the secondary delivery conduit 11D contaning pressurized breathable material. The interior surface 25C of the second side aperture 25A may also be sized and shaped as desired to facilitate a snug connection with various shapes and sizes of connectors with other conduits.

The secondary conduit 11D is shown in FIG. 1 interconnected to the primary conduit 11 between the humidifier 48 and the variable restrictor 42. However, the secondary delivery conduit 11D may also be connected directly to the humidifier 48 or as otherwise desired. The pressurized gas is supplied toward 11E, the second side port 25 through secondary variable restrictor 46 and pressure regulator 11F. The pressure regulator 11F may be preset or may be electrically operable by the microprocessor 45 via conductor 11G to supply gas at pressures between about 2 psi and about 25 psi and at high frequencies. In operation, the exhaust restrictor 42C is closed and the secondary variable restrictor 46 is open. The primary restrictor 42 may be open or closed.

FIG. 1 also shows a source of lung therapy material 11H such as medication (drugs) optionally adaptable into the system 10. That is, a source of breathable material that may be a liquid, an aerosol, a gas like nitric oxide or the like may be provided to pass via conduit 11J directly into conduit 11D to combine with air or in lieu of air. When source 11H is provided, the section 11K may not be connected to the primary conduit 11. Alternatively, restrictors (shown in phantom as 11L and 11M) electrically operated by microprocessor 45 via conductors (not shown to maintain clarity) may be added in section 11K as well as conduit 11J so that the lung therapy material may be supplied separately or with the gas. In operation, the restrictors 11L, 11M, 42 and 46 may be aligned to supply the lung therapy material with the beginning of a breath so that the gas flow carries the material to the lungs. The therapeutic material may also be delivered through the primary conduit 11 via conduit 11J and section 11K.

Referring back to FIG. 2, a ventilation conduit 27 is disposed between the second side aperture 25A and the central channel 26, allowing the flow of breathable material therethrough and directing pulses of gas toward the second port 23 and into the patient's trachea via the endotracheal tube 4. As can be seen, the ventilation channel 27 is sized to be smaller in cross-section than the second side aperture 25 and is here shown as a circular in cross-section channel that bends at elbow 27A toward second port 23. As can be seen, the inner portion 27B of the channel 27 has an axis 27C that intersects the axis 30 at an angle 27D that is here shown to be about 20 degrees. The angle 27D may vary from about 10 degrees to at least 45 degrees, but preferably is selected to facilitate directional flow of the material from conduit 10 through the second side aperture 25A and through ventilation channel 27 into the channel 26 and the stream of material flowing in channel 26. In this manner, rapid-pulses of gas are directed toward the patient through the second side aperture 25A and channel 27 to channel 26. The angle 27D also allows the momentum of the gas supplied through the ventilation conduit 27 to be cumulative with the momentum of the gas in the central channel 26. The increase in momentum is believed to increase the effectiveness of the ventilation effected in the patient.

The first side aperture 24A is also formed to have a conically tapered interior surface 24C having an inside diameter of about 3.5 mm at the outer end 25E of the first side port 24. The first side port 24 is sized and shaped to snugly and removably connect with monitoring conduit 14. Monitoring conduit 14 (FIG. 1) is connected to pressure monitoring means such as monitor 44 (e.g., an air pressure transducer). The conically tapered surface 24C of the first side aperture 24 may be shaped otherwise to facilitate snug interconnection with connectors of various shapes and sizes.

A pressure monitoring conduit 28 is formed in adapter 2 to extend between the first side aperture 24A and the central channel 26. The pressure monitoring channel 28 is here shown to be a circular in cross-section bore that extends along axis 28B to an elbow or intersection 28A. The pressure monitoring channel 28 has a lower portion 28F that extends along axis 28C toward the second port 23 to intersect axis 30 at an angle 28D which may vary from about 5 degrees to about 45 degrees and is here shown to be about 15 degrees. The pressure monitoring channel 28 is here shown extending from the elbow 28A toward the second port 23 a length 28E sufficient to reduce the effects of turbulence in channel 26 and to act as an orifice or restriction to limit or inhibit the flow of material from the channel 26 into conduit 14 while still permitting pressure signals to be transmitted promptly. That is, the lower portion 28F is shown smaller in cross-section from upper portion 28G to minimize the flow of material in and out but to allow the pressure changes in the material to be promptly communicated or reflected. Thus, the pressure in the patient's tracheal airway is communicated to the pressure monitoring means 44 which in turn provides a signal reflective of the pressure to the microprocessor 45 via a conductor 44A. The signal reflecting pressure is thereafter processed and transmitted to a separate display means via conductor 45B. The display 45A may be a video monitor controlled by the microprocessor to display a number reflective of the pressure detected. The display may also show waveforms that can be used to control the ventilator via the microprocessor. It should also be noted that the user may select tubing 14 of a particular length and cross section such that where coupled with pressure monitoring channel 28, they provide for desired fluid resistance or impedance and capacitance to facilitate interfacing with a selected microprocessor.

In the preferred embodiment of FIG. 2, the cross-sectional area of the ventilation channel 27 is larger than the cross-sectional area of the pressure monitoring channel 28. Additionally, the pressure monitoring channel 28 communicates with the central channel 26 at a position 28H which closer to the distal end 21 of the second port 23 than the position 27E at which the ventilation channel 27 communicates with the central channel 26. That is, the ventilation channel 27 enters the channel 26 at a distance 30C spaced from the entrance of pressure monitoring channel 28. The position of the pressure monitoring channel 28 relative to the position of the ventilation channel 28 permits the monitoring of pressure within the central channel 26 at a point which includes the combined pressures originating from the gas supplied through the ventilation conduit 27 and primary conduit 11.

Referring to FIGS. 7 through 12, an adaptor is shown having base 102 (FIG. 7) and a top 104 (FIG. 8) that are separately formed to be mated together into an adapter comparable to adapter 2 of FIG. 2.

The base 102 has a first port 105 for connection to a receiver such as receiver 8. The first port 105 is here shown to include a cylindrical portion 106 formed to sealingly connect to the receiver either by connection interior or exterior the cylindrical portion 106.

A collar 108 extends about the cylindrical portion 106 to present a flat seal surface 107. The collar 108 may be unitarily formed with the cylindrical portion 106. The inner end 110 is also unitarily formed with the cylindrical portion 106. The central channel 112 is formed on the axis 114 of base 102 and is in communication with the first port 105. The opening 112 extends to the interior 116 of the cylindrical portion 106 the receiver such as receiver to read 8. The cylindrical portion 106 snugly and sealingly receives a connector to interconnect the base 102 to the receiver.

The inner end 110 has a first groove 118 and a second groove 120 formed therein. The first groove 118 and the second groove are each radially spaced 122 from the other about 90 degrees and extend outwardly from the central channel 112 which is comparable to central channel 26 (FIG. 2).

Figure 9:
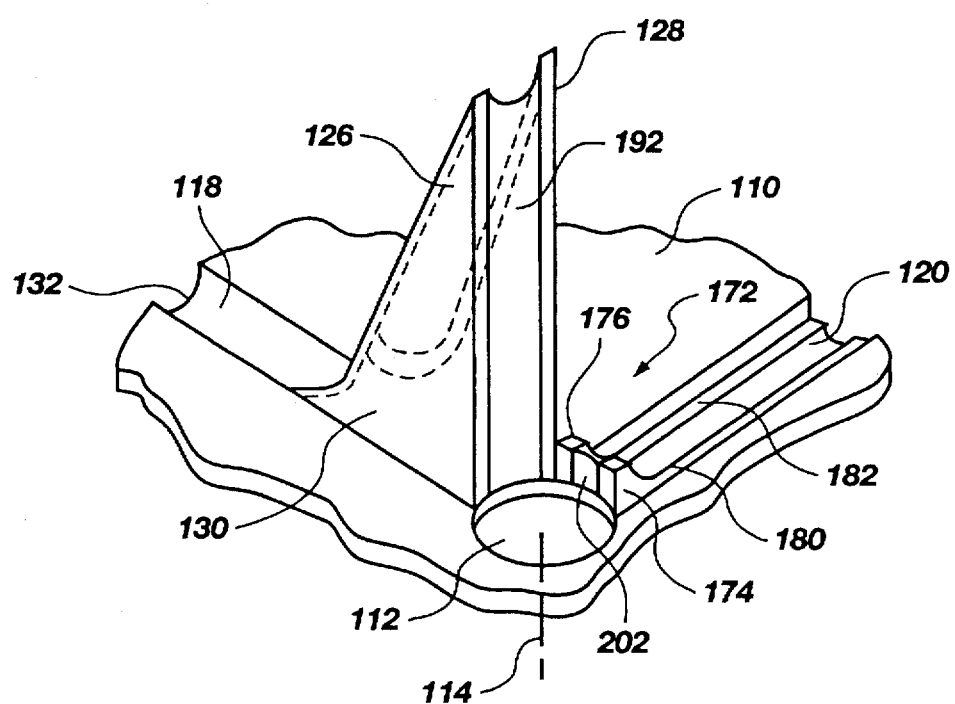
FIG. 9 is an enlarged partial cut-away of a portion of the base portion of FIG. 7.
Figure 10:
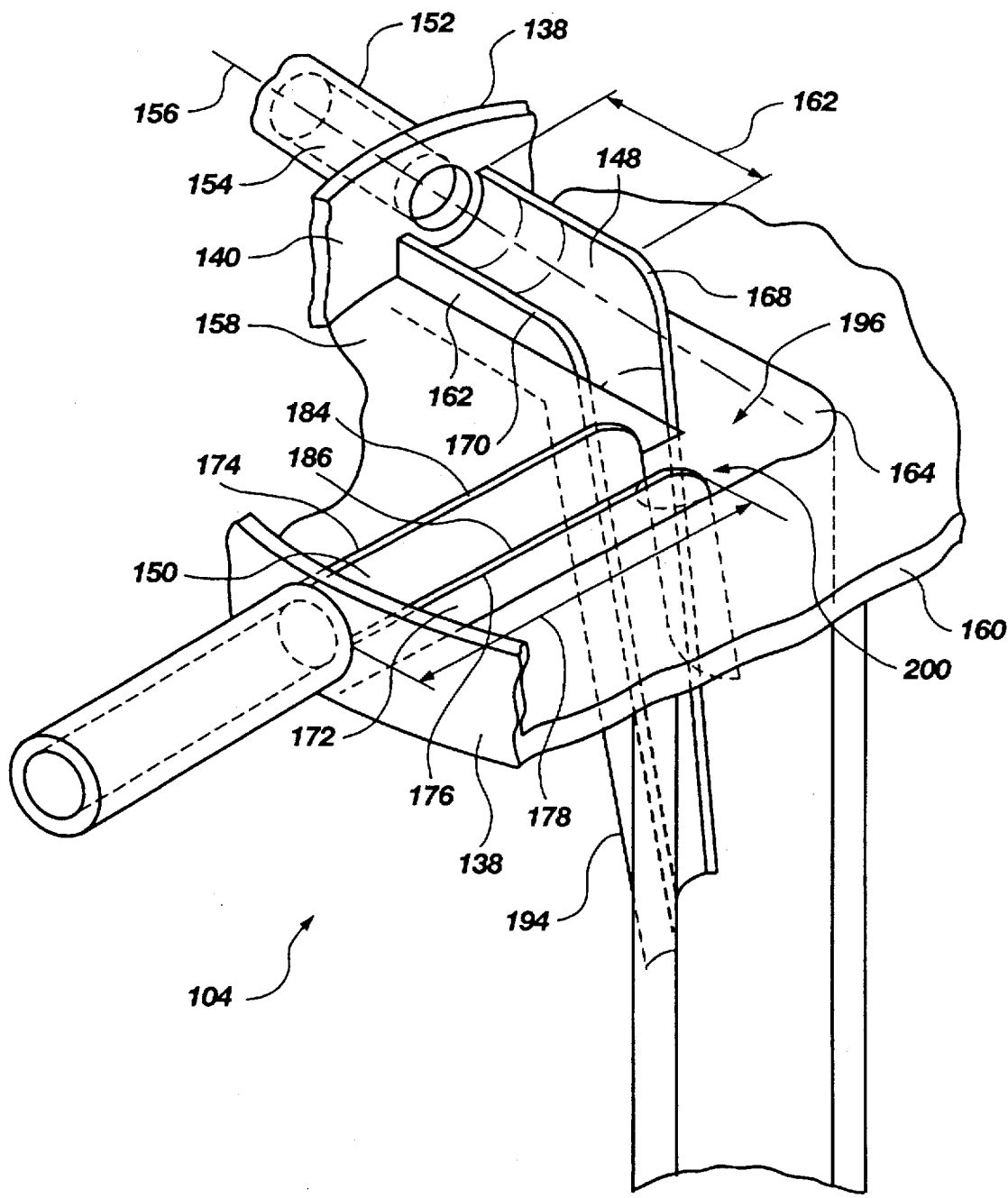
FIG. 10 is an enlarged partial rendition in perspective of portions of the top of FIG. 8.

The first groove 118 extends from the outer surface 124 of the cylindrical portion 106 inward toward an alignment member 126. As best seen in FIG. 9, the alignment member 126 has a left side 128 spaced apart from a right side 130. The groove 118 is bored or machined out of the inner end 110 and the alignment member. It may also be unitarily formed in the base 102. That is, the base 102 may be made from any convenient plastic-like material by molding. The mold may be formed to provide for the groove 118, as well as the groove 120 and the alignment member 126.

The groove 118 is here shown to be semicircular in cross section 132. When the top 104 and base 102 are assembled, the groove 118 is part of the channel for supplying material to the central channel 112 as discussed hereinafter.

Figure 8:
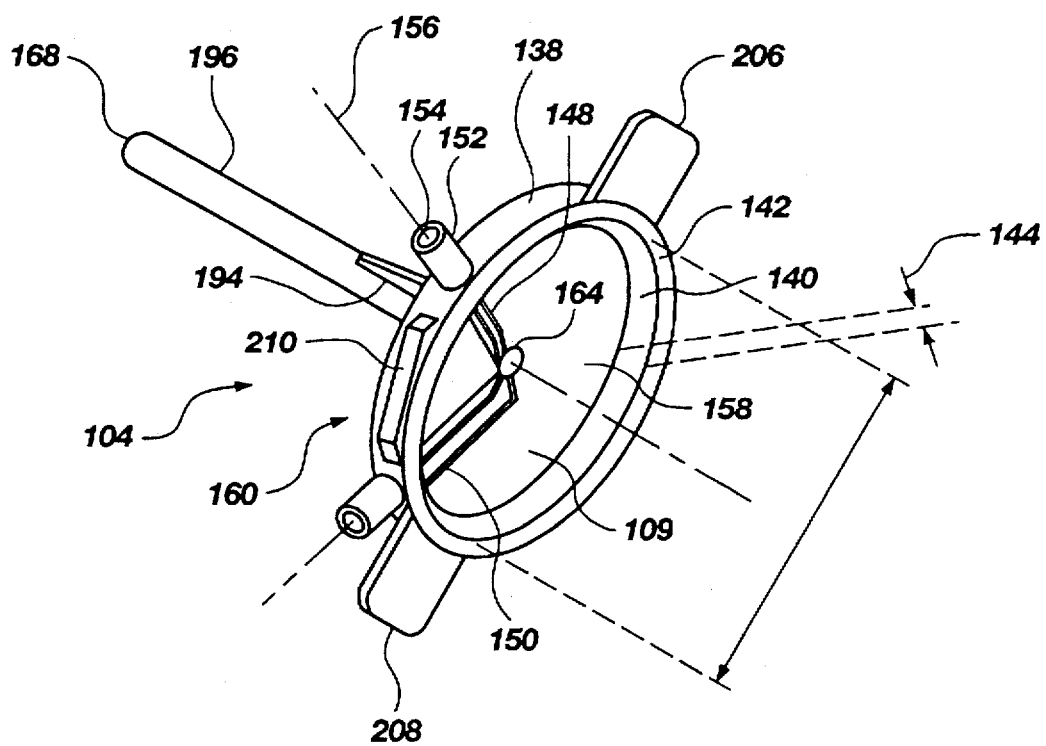
FIG. 8 is an enlarged perspective view of the top portion of an adapter for use with the present invention.

Turning to FIG. 8, the top 104 of the adapter is formed and configured to snugly mate with the base 102 to form an adaptor comparable to adapter 2 shown in FIG. 2 for use in a system such as that shown in FIG. 1.

The top 104 has an outer wall 138 that has an inner surface 140. The inner surface 140 is circular and sized to snugly slide over the outer surface 124 of the base 102 with a flat surface 142 formed and positioned to sealingly abut the flat surface 107 of collar 108. In final assembly, a sealing material or glue may be placed either on inner surface 140 or outer surface 124 to secure the base 102 and top 104 together as the surface 140 is urged against the surface 107 of collar 108. The resulting adapter will not leak air or other material. Joinder of the base 102 and top 104 may be effected by use of epoxy glues or similar compounds. However, any medically acceptable material that results in a sealing association is acceptable. In some cases, even plastic welding techniques may be available.

The top 104 is recessed a distance 144 which is longer than the distance 146 between the collar 108 and the inner end 110. The recess 109 functions as a receiver to connect with the connecting means of the base 102. The connecting means includes the outer surface 124, the alignment member 126 and finger 172. The distance 146 is carefully selected so that the grooves 118 and 120 sealingly mate or abut with corresponding grooves 148 and 150 as hereinafter discussed. The top 104 has a first side port 152, which is comparable to side port 24 of the adapter 2 in FIG. 2. The first side port 152 has a channel 154 that is circular in cross section and that extends inwardly along axis 156 to the groove 148. The groove 148 is formed on the inner surface 158 of the end cover 160. As better seen in FIG. 10, the groove 148 is formed in an elongated ledge 162 that extends from surface 140 inwardly toward the extension 164 of the central channel 112 by boring out a semicircular (in cross section) channel. The groove 148 is formed along axis 156 a distance 162 which equals distance 164 (FIG. 7) in the base 102 for groove 118. The ledge 162 arcs or bends downwardly and is formed with a smaller in diameter semicircular (in cross section) channel extending to intersect the interior wall 166 of the extension 164 of channel 112, which extends towards the second part 168.

Figure 11:
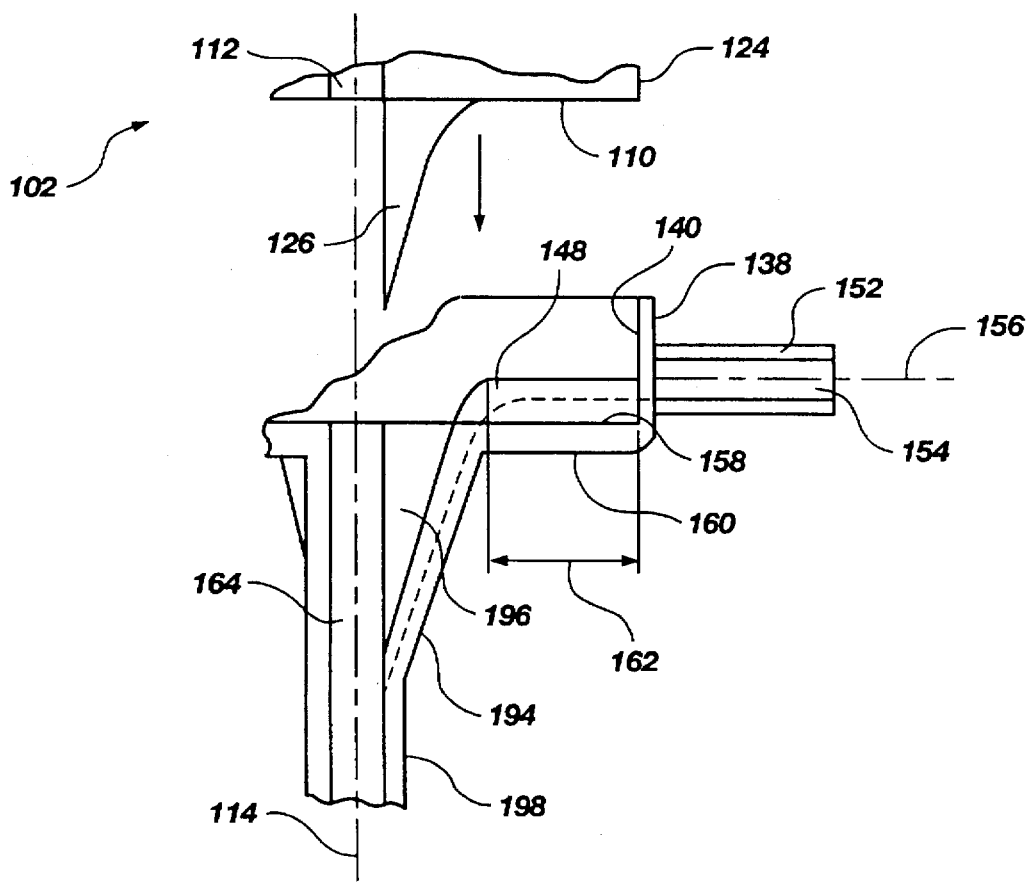

As can be seen in FIG. 11, upon mating the top 104 and the base 102, the alignment member 126 snugly seats against the left surface 168 and right surface 170 of the groove 148 to form a pressure monitoring channel comparable to pressure monitoring channel 28 of the adapter 2 of FIG. 2.

Figure 7:
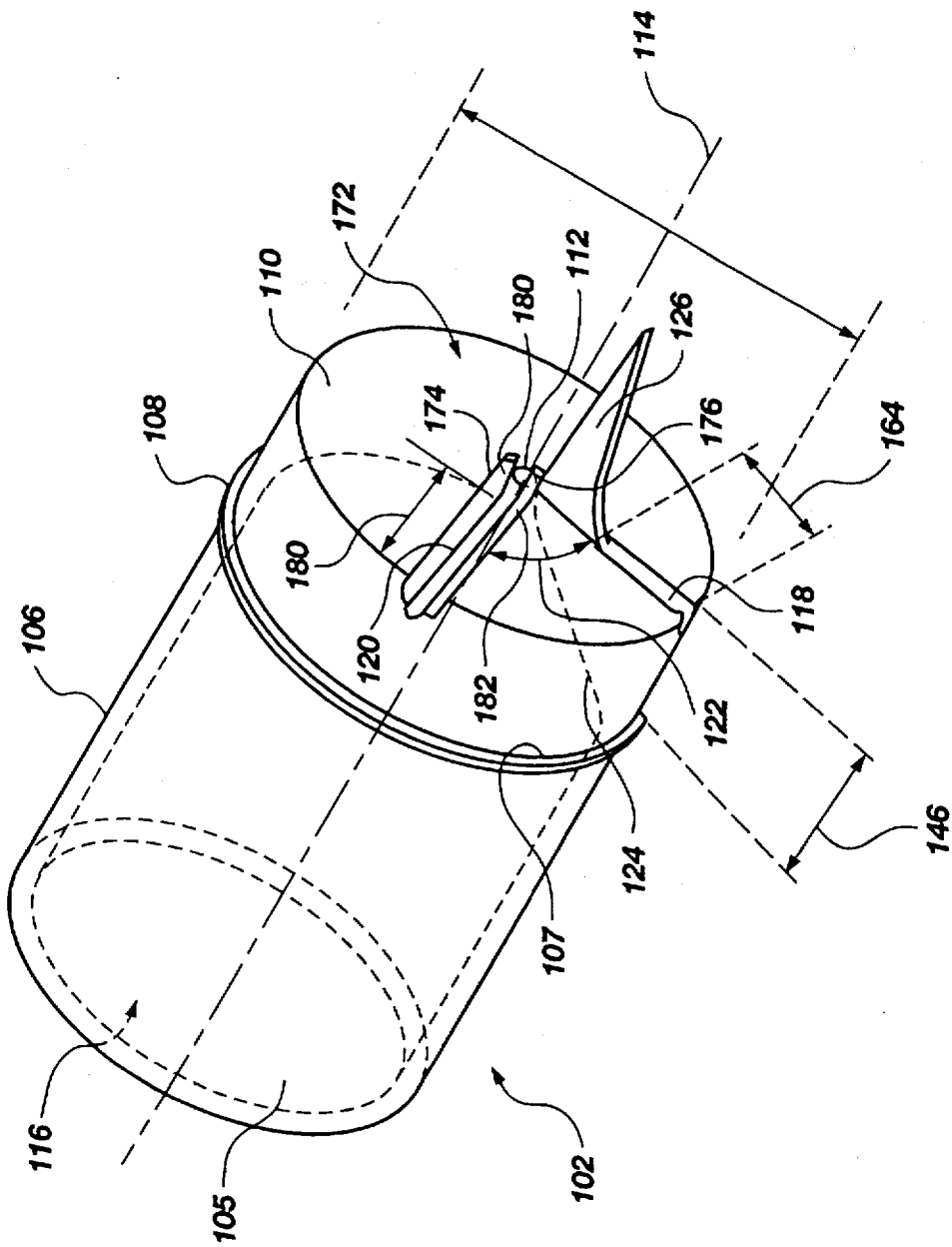
FIG. 7 is an enlarged perspective view of the base portion of an adapter for use with the present invention.

The top 104 has a second ledge 172, which extends inwardly from surface 140 toward the extension 164 of the central channel 112. The second ledge 172 also has a semicircular (in cross section) channel bored out to form a left surface 174 and a right surface 176. The channel functions as groove 150 and extends a distance 178 which is the same as distance 180 (FIG. 7). The top 104 is also formed of a material comparable to the material used to form the base 102.

Figure 12:
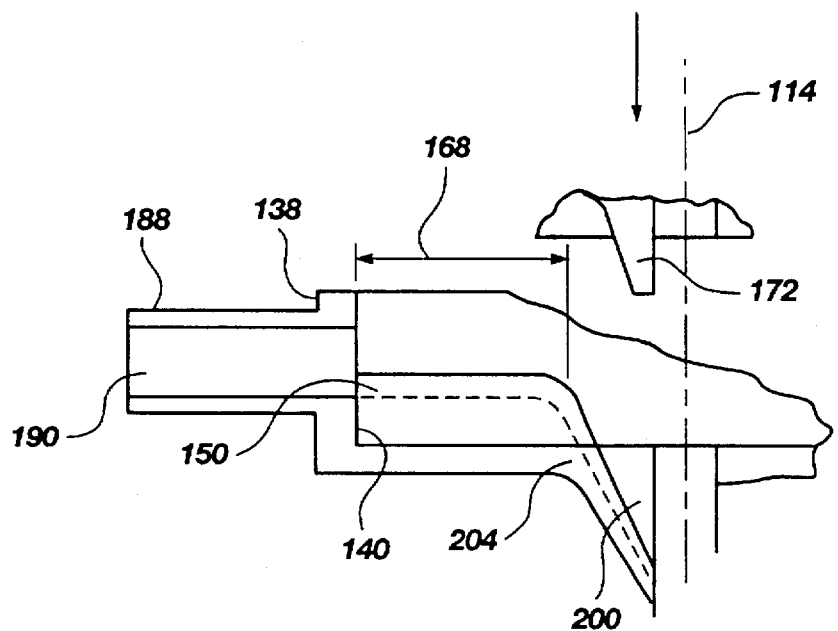
FIGS. 11 and 12 are partial side cut-away renditions of the top and base portions of FIGS. 7 and 8.

As better seen in FIGS. 9 and 12, the base 102 has an alignment finger 172 formed. The finger 172 has a left side 174 and a right side 176 with a semicircular channel thereinbetween. The finger 172 is sized and shaped with surfaces 180 and 182 which are positioned to mate snugly against surfaces 184 and 186 upon mating the top 104 with the base 102. Upon mating, the second ledge 172 and the groove 120 form a ventilation conduit comparable to ventilation conduit 27 of the adapter 2 of FIG. 2. That is, the second side aperture 188 has a circular in cross section channel 190 that communicates with grooves 120 and 150.

The alignment member 126 inserts into a comparably sized space in the top 104 as seen in FIG. 11. The alignment member 126 is here formed with an upright groove 192 that forms part of the extension 164 of center channel 112 when the alignment member 126 is in place in the assembled adapter. A stiffener 194 is provided in the top 104 to provide space to machine out a receptacle 196 for the alignment member 126 and to support the extension 198 with the extension channel 164 in it.

Similarly the alignment finger 172 inserts into comparably sized space 200. As seen in FIG. 9, it too has a sidewall 202 that becomes part of the sidewall of the extension 164 of the center channel 112 when mated as shown in FIG. 12. A web 204 is also provided in the top 104 to strengthen the extension 108 and to provide structure from which to machine space 200. When the base 102 and top 104 are mated, the center channel 112 and extension 164 are in alignment on axis 114.

Referring back to FIG. 9, the top 104 is also shown with extending flanges 206 and 208. The flanges 206 and 208 are unilaterally formed with the top 104 and are for grasping by a user. A flat surface 210 is provided with a corresponding flat surface, not shown, symmetrically opposite so that a wrench or other tool may be used to grasp the top and to grasp the adapter for manipulation thereof.

Figure 13:
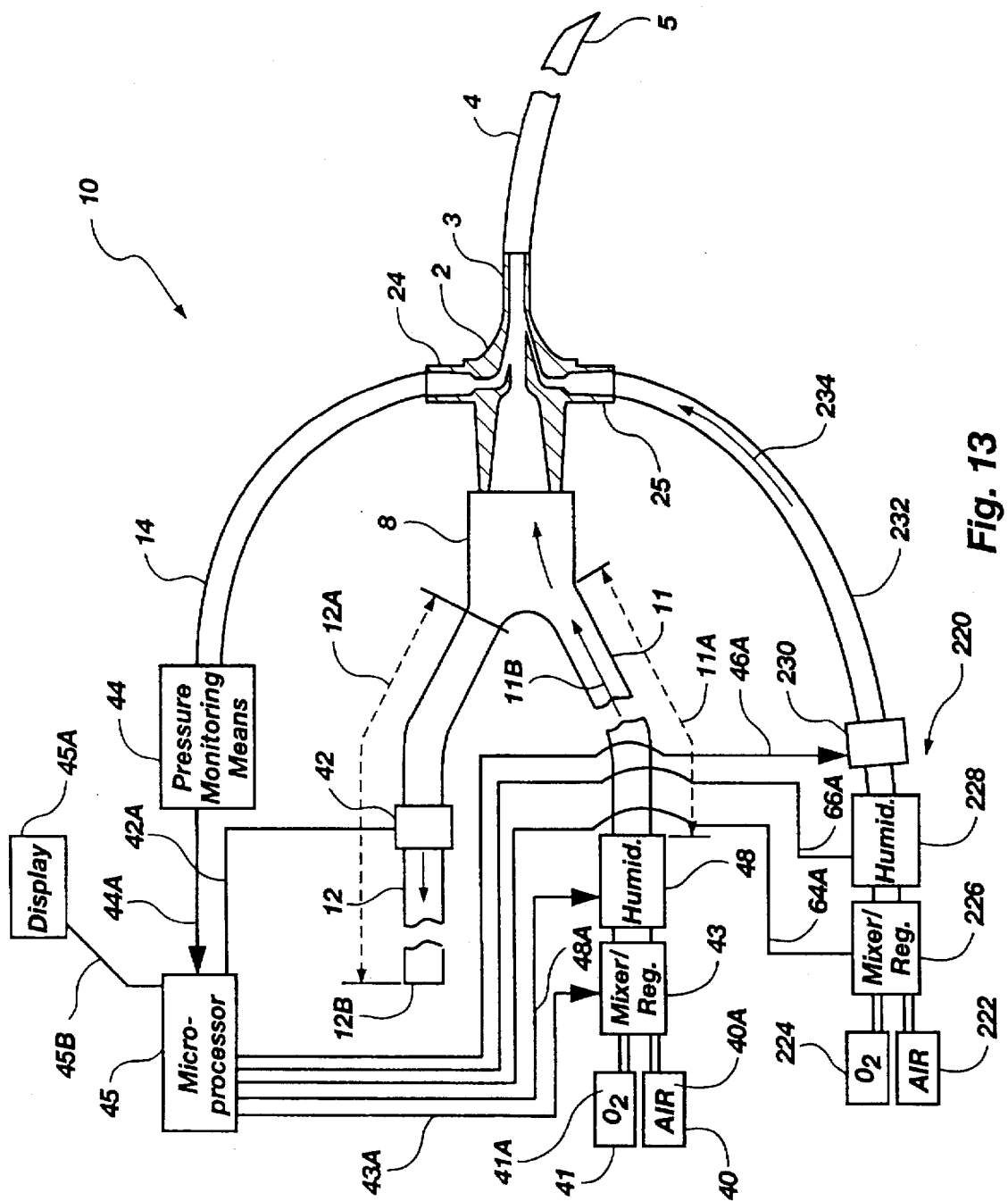
FIG. 13 is a schematic of an alternate ventilation system of the present invention.

In reference to FIG. 1, it may be noted that the source of air 40 and oxygen 41 act as the material source for both ventilation at conventional ventilate rates and at high frequency ventilation rates. In FIG. 13, an alternate arrangement is depicted in which a separate source is used for ventilation at high frequency ventilation rates. More specifically, the system of FIG. 13 also includes a high frequency jet ventilator (HFJV) portion 220 having air source 222 and oxygen source 224. A separate mixer and regulator 226 and a humidifier 228 are also provided and are substantially equivalent in form and function to their counterparts found in the conventional ventilator system previously described with respect to FIG. 1. The HFJV portion 220 includes a valve 230 which preferably operates under the control of microprocessor 45 via conductor 46A to regulate the gas flow rate through the secondary delivery conduit 232 toward 234 the adapter 2 and to provide high frequency ventilation at the rate of about 240 to 660 breaths per minute (4–11 breaths per second).

Ventilation at conventional ventilation rates, rapid-pulse ventilation rates, or a combination of conventional ventilation and rapid-pulse ventilation rates may be supplied by operating valve 250 and exhaust valve 42 in selected patterns as desired. Indeed, the microprocessor may be preprogrammed or may be operated to vary the rates and pressures as desired for a particular patient.

Using the system of FIG. 13, rapid-pulse ventilation is applied to a patient by supplying pressurized gases or breathable material via the second side aperture 25. Gas or breathable material at conventional ventilation rates is supplied via the first port 22. A combination of rapid-pulse and conventional ventilation rates is obtained by supplying gases simultaneously in an alternating pattern, or intermittently through both the secondary side aperture and the first port.

Figure 14:
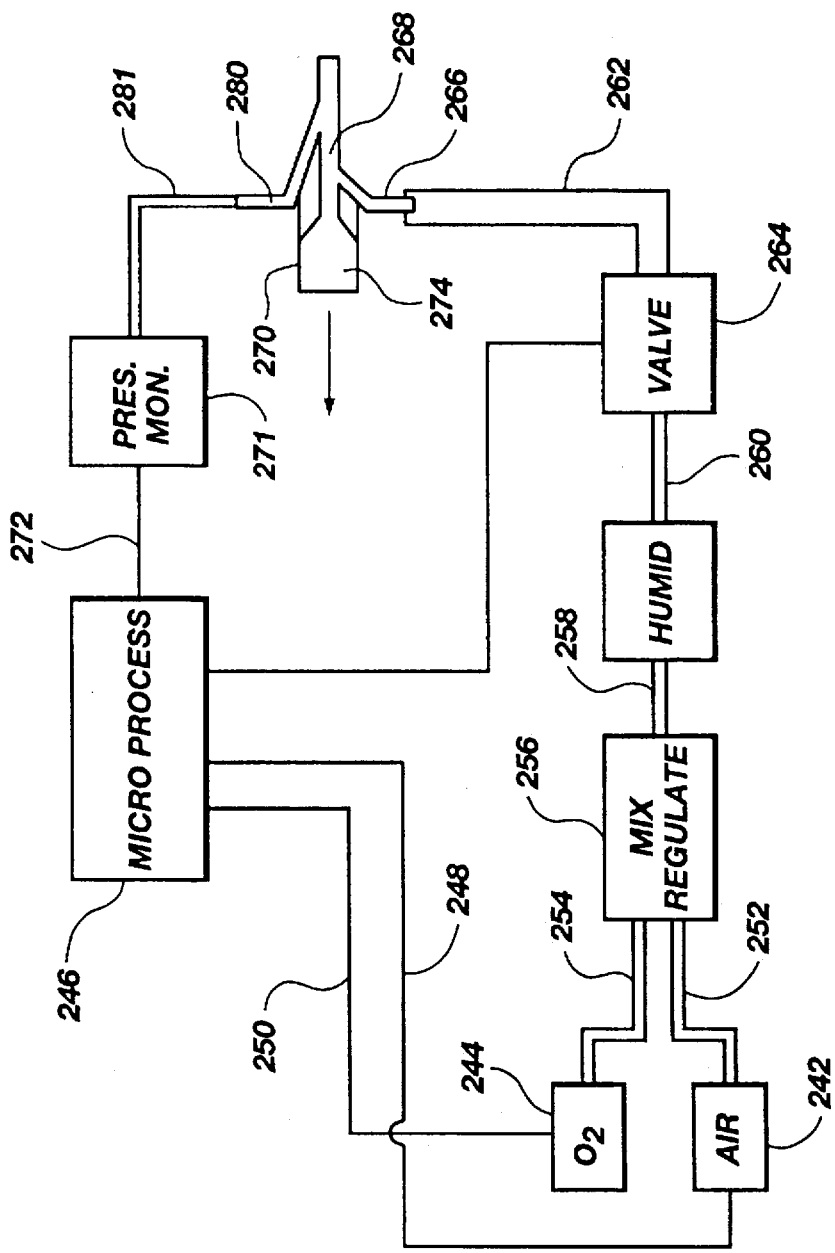
FIG. 14 is a schematic of an alternate ventilation system of the present invention.

In FIG. 14, a system is depicted in which conventional ventilation components are not provided. Rather, the adapter 240 (comparable to adapter 2) is used with other components to provide for high frequency or rapid pulse ventilation. Air is provided by source 242 and oxygen is provided by source 244. Air and oxygen are supplied in accordance with control signals supplied by the user via microprocessor 246 and conductors 248 and 250. The air and oxygen are supplied via conduits 252 and 254 as shown to a mixer and regulator 256. The mixer and regulator 246 mixes the supplied gases and regulates their output pressure as the mixture is supplied via conduit 258 to the humidifier. The humidifier humidifies the gas mixture which is supplied via conduits 260 and 262 through valve 264.

The valve 264 is controlled by the microprocessor 246 and supplies high frequency pulses to the patient via the second side aperture 266 and through the central channel 268 of the adapter 270. Pressure is detected by a pressure monitor 271 connected to sense pressure in the central channel 268 through the first side aperture 280 and conduit 281. Signals reflective of the sensed pressure are provided to the microprocessor 246 via conductor 272. The first port 274 is open to the atmosphere and may be used for connection to another ventilation system such as a conventional ventilation system.

In the alternative embodiment of FIG. 14, the high frequency and/or conventional ventilation is controlled by valve 264 and the adapter 270. The first port 274 of the adapter 2 is open to the atmosphere. Alternatively, a single conduit (such as exhaust conduit 12) may be coupled to the first port 22 in order to direct the exhaled and unused material away from the users and patient. A flowmeter may also be coupled to the first port 22.

It may also be noted that the rate of gas flowing (e.g., liters/minutes) through the second side aperture 24 in FIG. 1 and 266 in FIG. 14 can be calculated by measuring the difference between the gas pressure entering the second side aperture 24 and the pressure in the adapter 2 as sensed through the pressure monitoring channel 28 or 280. Additionally, the rate of gas (e.g., liters/minute) from primary conduit 11 (FIG. 1) and conduit 262 (FIG. 14) can be calculated using differential pressures. The combined gas flow rate calculations are used to monitor total volumes of gas delivered to the patient with each breath and over time.

FIG. 3 is a slightly modified embodiment of the adapter 2 with a first port 22', a second port 23', a second side aperture 25', and a first side aperture 24'. As shown, internal surface 32' of the first port as well as the internal surfaces 24C' and 25C' are all circular in cross-section forming a cylindrical opening.

FIG. 4 is a frontal view of the adapter 2, wherein the second side aperture 25 is radially spaced apart from the first side aperture 24 as hereinbefore stated. Ports 24 and 25 are formed to extend from the exterior surface 38, which is formed by an end wall of the first port 22. Two tabs 50A and 50B are formed to extend outward from exterior 38 to facilitate handling and labeling of the adapter 2.

FIG. 5 is a slightly modified embodiment of the adapter 2 shown in ports 52 and 54 formed with a male-threaded connector (such as a "Luer-Lock" connector) 32 for interconnection to conduits or tubes. When threaded connector tip 32 is securely fastened to a reciprocally matching male or female connector in a connecting conduit, the formed connection will provide a snug fit that inhibits disassociation and gas leakage. Port 33 is tapered to frictionally accept and retain a conduit or tube 33A.

In operation, the described ventilation systems deliver breathable material (e.g., air and oxygen) to a patient and allow the user to monitor airway pressure within a single, compact adapter unit. There is no need for special endotracheal tubes that contain connecting tubes and pressure monitoring side lumens or the like. The user may also operate a microprocessor to develop ventilation modalities that are a combination of high frequency gas pressure pulses and conventional ventilation pulses.

Figure 6:
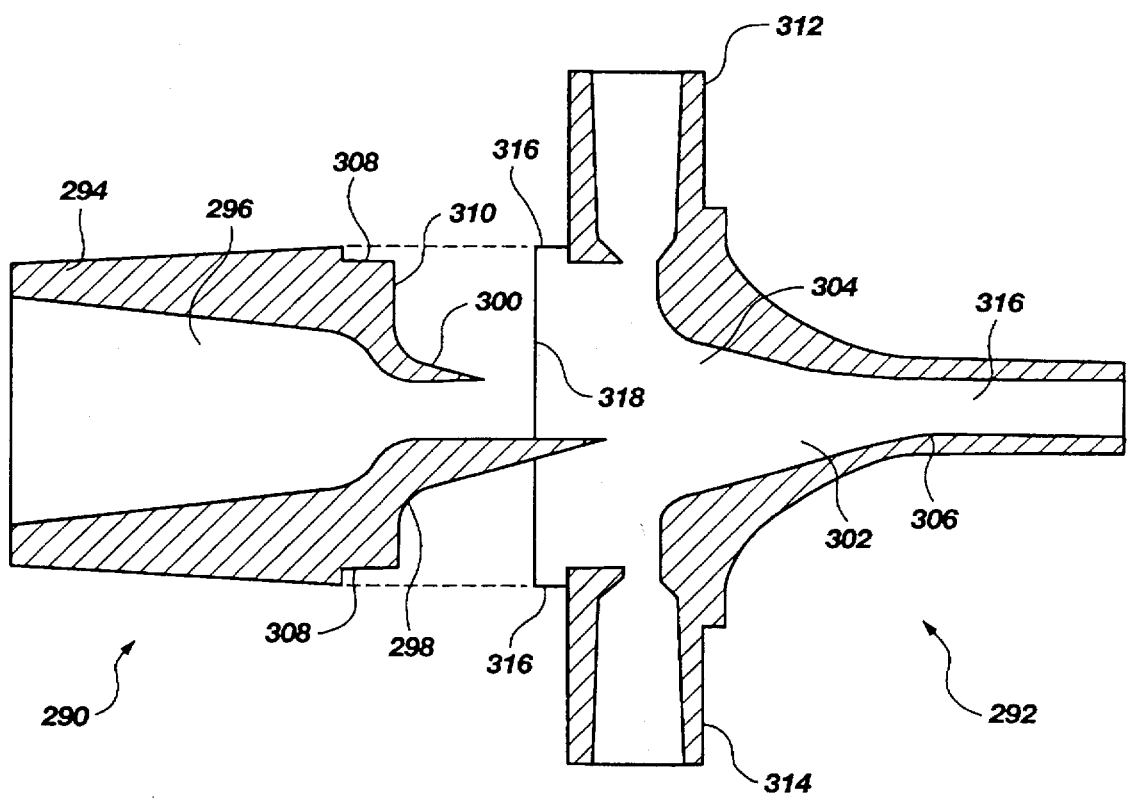
FIG. 6 is a cross-sectional diagram of the adapter of FIG. 2, illustrating two members of the adapter prior to assembly.

FIG. 6 is a cross-sectional view of the adapter of FIG. 2, further illustrating a simplified two-piece assembly of the adapter. The two-piece assembly includes a base 290 and a top 292. The base 290 includes the first end 294 formed to define the first port 296. The alignment member 298 and alignment finger 300 are provided to register with the top 292 and to form pressure monitoring channel 302 and high frequency ventilation channel 304 with the side wall 306. Recessed member is also included to assist in orienting and coupling base 290 to top 292. Recessed member 308 is here shown to encircle an insertable end 310 of the base 290.

The top 292 includes side ports 312 and 314 and end port 316. A lip 316 is also included on end 318 of the top 292 to snugly and sealingly fit over recessed member 308. The base 290 and the top 292 can be coupled by applying a suitable adhesive or by any other suitable means known in the art.

The adapter of the invention is preferably fabricated and molded from carbon chain polymers, examples of which include vinyl polymers and acrylic polymers. Many other suitable materials having desirable characteristics for the adapter (strength, impact-resistance, transparency, etc.) are also known in the art.

The adapter 2 is preferably injection-molded using at least one master mold defining outer adapter dimensions of varying sizes and configurations, and having relocatable internal segments to define different lengths, widths, and angled shapes of the ports (22, 24, and 25), side apertures (24A and 25A), the conduit 11, and the channels (27 and 28).

While specific embodiments of the invention have been shown and described in detail to illustrate the application of the principles of the invention, it will be understood that the invention may be embodied otherwise without departing from such principles.

What is claimed is:

1. A ventilation system for use in ventilating a patient, said ventilation system comprising:

a source of pressurized gas;

a primary delivery conduit connected to and in fluid communication with said source for receiving said pressurized gas from said source and transmitting said pressurized gas;

an endotracheal tube having an internal end for placement in the trachea of said patient and an external end opposite said internal end for positioning outside of the patient;

an adapter having a first end sealingly connectable to said primary delivery conduit and a second end sealingly connectable to said external end of said endotracheal tube, said first end having a first port formed therein for receiving said pressurized gas from said primary delivery conduit, said second end having a second port formed therein to transmit said gas to and for receiving exhaled gas from said patient through said endotracheal tube, said adapter having a central channel disposed between and in fluid communication with said first port and said second port, and said adapter having a first side aperture and a second side aperture spaced away from said first side aperture, said first side aperture and said second side aperture each being in fluid communication with said central channel;

an exhaust conduit for transporting gas exhaled by the patient away from said adapter, said exhaust conduit having two ends, one end of which is connectable to be in fluid communication with said first port;

pressure detecting means in fluid communication with said first side aperture to detect the pressure of any gas in said central channel and to generate signals reflective of the pressure of said gas in said central channel; and indicating means associated with said pressure detecting means to receive said signals and to visually display an indication of the detected pressure of said gas in said central channel.

2. A ventilation system according to claim 1 further including control means coupled to said primary delivery conduit for selectively varying the flow rate of said pressurized gas through said first port.

3. A ventilation system according to claim 2, wherein said control means comprises a secondary delivery conduit coupled between said primary delivery conduit and said second side aperture for delivering gas under pressure from the primary delivery conduit to the endotracheal tube, valve means disposed in said secondary delivery conduit and responsive to control signals for varying the pressure of gas flowing through the secondary delivery conduit and said endotracheal tube, and signal means for selectively producing control signals for supplying said control signals to said valve means to operate said valve means to vary the pressure of said gas in said secondary delivery conduit.

4. A ventilation system according to claim 1 further including variable restrictor means disposed in said primary delivery conduit for setting a base flow rate of said pressurized gas through said primary delivery conduit and said adapter.

5. A ventilation system according to claim 1, wherein said one end of said exhaust conduit is connectable to be in fluid communication with said primary delivery conduit.

6. A ventilation system according to claim 1, wherein said source supplies pulses of gas and said second side aperture receives and communicates said pulses of gas to said adapter for further communication to said second port.

7. A ventilation system according to claim 1, wherein said central channel has an axis and said first side aperture and said second side aperture are each positioned radially apart about the axis of said central channel.

8. A ventilation system according to claim 6 further including a ventilation conduit disposed between and in fluid communication with said second side aperture and said central channel.

9. A ventilation system according to claim 8, wherein said ventilation conduit is positioned to direct said pulses of gas toward said endotracheal tube via said second port.

10. A ventilation system according to claim 9, wherein said ventilation conduit has a portion with an axis that intersects said axis of said central channel at a ventilation conduit angle.

11. The ventilation system according to claim 10, wherein said ventilation conduit angle is from about 10 degrees to about 45 degrees.

12. The ventilation system according to claim 11, further including a pressure monitoring conduit disposed between and in fluid communication with said first side aperture and said central channel, said pressure monitoring conduit being positioned to communicate said gas in said central channel to said pressure detecting means.

13. The ventilation system according to claim 12, wherein said pressure monitoring conduit communicates with said central channel at a position closer to said second port in relation to the point of communication between said ventilation conduit and said central channel.

14. The ventilation system according to claim 13, wherein said pressure monitoring conduit has a portion with an axis that intersects said axis of said central channel at a pressure conduit angle.

15. The ventilation system according to claim 14, wherein said pressure conduit angle is from about 5 to about 45 degrees measured between the axis of the central channel and the axis of the pressure monitoring conduit.

16. The ventilation system according to claim 15, wherein said pressure monitoring conduit is angled toward said second port.

17. The ventilation system according to claim 16, wherein the cross-sectional area of ventilation conduit is larger than the cross sectional area of said pressure monitoring conduit.

18. A ventilation system according to claim 8, further including a locking mechanism connected to said second side aperture for securely associating said source to said second side aperture and a second outer edge extending from said second side aperture to securely receive said locking mechanism for securing said source.

19. A ventilation system according to claim 10, wherein said locking mechanism consists of a threaded connecting device.

20. A ventilation system according to claim 1, further including a pressure monitoring conduit disposed between and in fluid communication with said first side aperture and said central channel, said pressure monitoring conduit being positioned to communicate said gas in said central channel to said pressure detecting means.

21. A ventilation system according to claim 20, further including a locking mechanism connected to said pressure detecting means for securely associating said pressure detecting means to said first side aperture and a first outer edge extending from said first side aperture to securely receive said locking mechanism for securing said pressure monitoring means.

22. A ventilation system according to claim 21, wherein said pressure monitoring conduit communicates with said central channel at a position closer to said second port in relation to the point of communication between said ventilation conduit and said central channel.

23. The ventilation system according to claim 22, wherein said pressure monitoring conduit has a portion with an axis that intersects said axis of said central channel at a pressure conduit angle.

24. The ventilation system according to claim 23, wherein said pressure conduit angle is form about 5 to about 45 degrees measured between the axis of the central channel and the axis of the pressure monitoring conduit wherein said pressure monitoring conduit is angled toward said second port.

25. A ventilation system according to claim 24, wherein the cross-sectional area of said ventilation conduit is larger than the cross-sectional area of said pressure monitoring conduit.

26. The ventilation system according to claim 1, wherein said adapter has a base and a top and connection means for connecting said base to said top, and wherein said base is formed to have said first port and said central channel.

27. The ventilation system according to claim 26, wherein said top has said second port, said first side aperture, said second side aperture and receiving means for receiving said connection means of said base.

28. The ventilation system according to claim 27, wherein said connection means includes means to align the base with the top.

29. The ventilation system according to claim 28, wherein said central channel has an axis and said first side aperture and said second side aperture are each positioned radially apart about the axis of said central channel.

30. The ventilation system according to claim 29, wherein said adapter has a ventilation conduit disposed between and in fluid communication with said second side aperture and said central channel.

31. The ventilation system according to claim 30, wherein said ventilation channel is formed of a groove in said base and a groove in said top which register with each other with said top and said base fully assembled.

32. The ventilation system according to claim 31, wherein said means to align the base with top includes an alignment member extending outwardly from said base and a recess extending inwardly in said top sized to receive said alignment member.

33. The ventilation system according to claim 32, further including a pressure monitoring conduit disposed between and in fluid communication with said first side aperture and said central channel, said pressure monitoring conduit being positioned to communicate said gas in said central channel to said pressure detecting means.

34. The ventilation system according to claim 33, wherein said pressure monitoring conduit has a portion with an axis that intersects said axis of said central channel at a pressure conduit angle.

35. The ventilation system according to claim 34, wherein said pressure monitoring conduit is angled toward said second port.

36. The ventilation system according to claim 35, wherein said pressure monitoring conduit is formed by a groove in said base and a groove in said top which register with each other with said top and said base fully assembled.

37. The ventilation system according to claim 36, wherein said means to align the base with the top includes an alignment finger extending away from said base and a finger recess in said top sized to receive said finger.

38. The ventilation system of claim 1, wherein said exhaust conduit is mechanically associated with said first end to be in fluid communication therewith, and wherein said ventilation system includes a source of lung therapy material and a conduit connected to and between said source of lung therapy material and said adapter to supply lung therapy material there between.

39. A method of making an adapter for use in a ventilation system for connection to an endotracheal tube, said method comprising:

forming a base with a first port for sealing connection to a source of gas, a central channel for communicating said gas away from said first part and connection means for connecting said base to a top;

forming said top to have a second port for connection to an endotracheal tube, a first side port, a second side port and receiving means to receive the connecting means of said base;

forming a first groove in said base and a first groove in said top to be in registration upon full assembly of said base and said top to define a channel communicating between said first side port and said central channel;

forming a second groove in said base and a second groove in said top to be in registration upon full assembly of said base and said top to define a channel communicating between said second side port and said central channel;

providing alignment means in association with said top and said base to align said top and base; and assembling said top and said base.

40. The method of claim 39, further including providing bonding material and bonding said base and said top.

41. The method of claim 40, wherein said alignment means includes an alignment member on said base and a corresponding alignment recess in said top.

42. A ventilation system for use in ventilating a patient, said ventilation system comprising:

a source of pressurized gas;

a delivery conduit connected to and in fluid communication with said source for receiving said pressurized gas from said source and transmitting said pressurized gas;

an endotracheal tube having an internal end for placement in the trachea of said patient and an external end opposite said internal end for positioning outside of the patient;

an adapter having a first end open to the atmosphere and a second end sealingly connectable to said external end of said endotracheal tube to transmit said pressurized gas to said patient through said endotracheal tube, said adapter having a central channel, a first side aperture and a second side aperture spaced away from said first side aperture, said first side aperture and said second side aperture each being in fluid communication with said central channel, said second side aperture being connectable to said delivery conduit to receive and transmit said pressurized gas toward said endotracheal tube through said central channel;

pressure detecting means in fluid communication with said first side aperture to detect the pressure of any gas in said central channel and to generate signals reflective of the pressure of said gas in said central channel; and indicating means associated with said pressure detecting means to receive said signals and to visually display an indication of the detected pressure of said gas in said central channel.

43. The ventilation system of claim 42, wherein said first end is formed for connection to a conduit to receive pressurized gas for transmission to said central channel.

44. The ventilation system of claim 43, further including a source of lung therapy material and further including a conduit connected to supply said lung therapy material into the pressurized gas.

45. A ventilation system for use in ventilating a patient, said ventilation system comprising:

a first source of pressurized gas;

a second source of pressurized gas;

a first delivery conduit connected to and in fluid communication with said source for receiving said pressurized gas from said first source and transmitting said pressurized gas;

a second delivery conduit connected to and in fluid communication with said source and for receiving said pressurized gas from said second source and transmitting said pressurized gas;

an endotracheal tube having an internal end for placement in the trachea of said patient and an external end opposite said internal end for positioning outside of the patient;

an adapter having a first end sealingly connectable to said first delivery conduit and a second end sealingly connectable to said external end of said endotracheal tube, said first end having a first port formed therein for receiving said pressurized gas from said first delivery conduit, said second end having a second port formed therein to transmit said gas to and for receiving exhaled gas from said patient through said endotracheal tube, said adapter having a central channel disposed between and in fluid communication with said first port and said second port, and said adapter having a first side aperture and a second side aperture spaced away from said first side aperture, said first side aperture and said second side aperture each being in fluid communication with said central channel, and said second side aperture being connected to second delivery conduit to receive pressurized gas therefrom for transmission to said central conduit;

an exhaust conduit for transporting gas exhaled by the patient away from said adapter, said exhaust conduit having two ends, one end of which is connectable to be in fluid communication with said first port;

pressure detecting means in fluid communication with said first side aperture to detect the pressure of any gas in said central channel and to generate signals reflective of the pressure of said gas in said central channel; and indicating means associated with said pressure detecting means to receive said signals and to visually display an indication of the detected pressure of said gas in said central channel.

46. An adapter for use in a ventilation system, said adapter comprising:

a first end sealingly connectable to a primary delivery conduit to receive pressurized gas therefrom and a second end sealingly connectable to an external end of an endotracheal tube;

a first port formed in said first end for receiving said pressurized gas from said primary delivery conduit;

a second port formed in said second end to transmit said pressurized gas to and for receiving exhaled gas through said endotracheal tube;

a central channel disposed between and in fluid communication with said first port and said second port;

a first side aperture in fluid communication with said central channel for connection to pressure detecting means to detect the pressure of any gas in said central channel and to generate signals reflective of the pressure of said gas in said central channel;

an exhaust conduit for transporting gas exhaled by the patient away from said adapter, said exhaust conduit having two ends, one end of which is connectable to be in fluid communication with said first port;

a second said aperture spaced away from said first side aperture and connectable to a secondary delivery conduit to receive and to transmit pressurized gas to said central channel; and indicating means associated with said pressure detecting means to receive said signals and to visually display an indication of the detected pressure of said gas in said central channel.

47. A method of delivering gas pressure pulses to assist respiration in a patient comprising the steps of:

providing a source of pressurized gas for supplying gas to said patient;

providing a primary delivery conduit and connecting said delivery conduit to be in fluid communication with said source, for transporting said pressurized gas to the patient;

providing an adapter and connecting said adapter to be in fluid communication with said primary delivery conduit, said adapter having two ends, a first port disposed at a first end of said adapter for connecting said primary delivery conduit to said adapter and for receiving gas from said primary delivery conduit and for carrying away gas exhaled by the patient, a second port disposed at a second end of said adapter, a central channel being disposed between and in fluid communication with said first port and said second port, and two side apertures being in fluid communication with said central channel;

providing an endotracheal tube in fluid communication with said second port for transmitting said gas to and for receiving exhaled gas from said patient, said endotracheal tube having an external end and having an internal end for placement in the trachea of said patient;

providing an exhaust conduit having two ends, one end of which is connectable to be in fluid communication either with said first port or with said primary delivery conduit, said exhaust conduit provided to transport gas exhaled by the patient away from said adapter;

providing a pressure detection means mechanically associated and in fluid communication with said first side aperture to sense pressure and generate signals reflective of the pressure of gas in central channel;

providing an indicating means associated with said pressure detecting means to receive said signals and to visually display an indication of the detected pressure of said gas in said central channel;

supplying gas under pressure through a second of said two side ports to provide high frequency ventilation;

supplying gas under pressure to said first port to provide conventional respiration.

48. An adapter for use in a ventilation system for use in ventilating a patient, said adapter comprising:

a first end having a first port sealingly connectable to a source of pressurized gas;

a second end having a second end sealingly connectable to an external end of an endotracheal tube;

a central channel disposed between and in fluid communication with said first port and said second port; and a first side aperture formed and positioned to be in fluid communication with said central channel and with pressure detecting means for detecting the pressure of any gas in said central channel.

49. A ventilation system for use in ventilating a patient, said ventilation system comprising:

a source of pressurized gas;

a primary delivery conduit connected to and in fluid communication with said source for receiving said pressurized gas from said source and transmitting said pressurized gas;

an endotracheal tube having an internal end for placement in the trachea of said patient and an external end opposite said internal end for positioning outside of the patient;

an adapter having a first end sealingly connectable to said primary delivery conduit and a second end sealingly connectable to said external end of said endotracheal tube, said first end having a first port formed therein for receiving said pressurized gas from said primary delivery conduit, said second end having a second port formed therein to transmit said gas to and for receiving exhaled gas from said patient through said endotracheal tube, said adapter having a central channel disposed between and in fluid communication with said first port and said second port, and said adapter having a first side aperture and a second side aperture spaced away from said first side aperture, said first side aperture and said second side aperture each being in fluid communication with said central channel;

an exhaust conduit for transporting gas exhaled by the patient away from said adapter, said exhaust conduit having two ends, one end of which is connectable to be in fluid communication with said first port;

pressure monitoring conduit disposed between and in fluid communication with said first side aperture and said central channel;

pressure detecting means in fluid communication with said pressure monitoring conduit to detect the pressure of any gas in said central channel and to generate signals reflective of the pressure of said gas in said central channel;

indicating means associated with said pressure detecting means to receive said signals and to visually display an indication of the detected pressure of said gas in said central channel; and a locking mechanism connected to said pressure detecting means for securely associating said pressure detecting means to said first side aperture and a first outer edge extending from said first side aperture to securely receive said locking mechanism for securing said pressure monitoring means.

50. A ventilation system for use in ventilating a patient, said ventilation system comprising:

a source of pressurized gas;

a primary delivery conduit connected to and in fluid communication with said source for receiving said pressurized gas from said source and transmitting said pressurized gas;

an endotracheal tube having an internal end for placement in the trachea of said patient and an external end opposite said internal end for positioning outside of the patient;

an adapter having
- a first end sealingly connectable to said primary delivery conduit, said first end having a first port formed therein for receiving said pressurized gas from said primary delivery conduit,
- a second end sealingly connectable to said external end of said endotracheal tube, said second end having a second port formed therein to transmit said gas to and for receiving exhaled gas from said patient through said endotracheal tube,
- a central channel disposed between and in fluid communication with said first port and said second port,
- a first side aperture and a second side aperture spaced away from said first side aperture, said first side aperture and said second side aperture each being in fluid communication with said central channel,
- a base and a top with connection means for connecting said base to said top, said connecting means including means to align said base with said top, said base being formed to have said first port and said central channel, said top being formed with said second port, said first side aperture, said second side aperture and receiving means, said receiving means being configured for receiving said connection means of said base;

an exhaust conduit for transporting gas exhaled by the patient away from said adapter, said exhaust conduit having two ends, one end of which is connectable to be in fluid communication with said first port;

pressure detecting means in fluid communication with said first side aperture to detect the pressure of any gas in said central channel and to generate signals reflective of the pressure of said gas in said central channel; and indicating means associated with said pressure detecting means to receive said signals and to visually display an indication of the detected pressure of said gas in said central channel.

51. A method of making an adapter for use in a ventilation system for connection to an endotracheal tube, said method comprising:

forming a base with a first port for sealing connection to a source of gas, a central channel for communicating said gas away from said first part and connection means for connecting said base to a top;

forming said top to have a second port for connection to an endotracheal tube, a first side port, a second side port and receiving means to receive the connecting means of said base;

forming a first groove in said base and a first groove in said top to be in registration upon full assembly of said base and said top to define a channel communicating between said first side port and said central channel;

forming a second groove in said base and a second groove in said top to be in registration upon full assembly of said base and said top to define a channel communicating between said second side port and said central channel;

providing alignment means in association with said top and said base to align said top and base;

providing bonding material for bonding said base to said top; and bonding said base to said top.

* * * * *